(12) United States Patent
Hallam

(10) Patent No.: US 7,449,053 B2
(45) Date of Patent: Nov. 11, 2008

(54) AIR FILTRATION DEVICE

(76) Inventor: David Richard Hallam, 286 Hyde Road, Denton, Manchester (GB) M34 3EH ( * ) Notice: Subject to any disclaimer, the term of this patent is extended or adjusted under 35 U.S.C. 154(b) by 362 days.

(21) Appl. No.: 10/565,428

(22) PCT Filed: Jul. 19, 2004

(86) PCT No.: PCT/GB2004/003140

§ 371 (c)(1),
(2), (4) Date: Jan. 18, 2006

(87) PCT Pub. No.: WO2005/011845

PCT Pub. Date: Feb. 10, 2005

(65) Prior Publication Data

US 2007/0086932 A1    Apr. 19, 2007

Related U.S. Application Data

(60) Provisional application No. 60/577,952, filed on Jun. 8, 2004.

(30) Foreign Application Priority Data

| Jul. 18, 2003 | (GB) | ................................. 0316837.4 |
| Apr. 29, 2004 | (GB) | ................................. 0409547.7 |
| May 13, 2004 | (GB) | ................................. 0410648.0 |

(51) Int. Cl.
*B03C 3/82* (2006.01)

(52) U.S. Cl. .................... 96/52; 95/58; 96/74; 96/95

(58) Field of Classification Search .............. 96/52, 96/74, 95–97, 223, 224; 422/186.07, 186.1; 95/58
See application file for complete search history.

(56) References Cited

U.S. PATENT DOCUMENTS

| 906,468 A | 12/1908 | Steynis |
| 1,157,859 A | 10/1915 | Freet |
| 1,454,219 A | 5/1923 | Goedicke |
| 1,505,669 A | 8/1924 | Quain |

(Continued)

FOREIGN PATENT DOCUMENTS

CA          1256284          6/1989

(Continued)

OTHER PUBLICATIONS

Rapid Communication article *Gas Phase Corona Discharges for Oxidation of Phenol in an Aqueous Solution*, by W.F.L.M. Hoeben, E. M. vanVeldhuizen, W. R. Rutgers and G. M. W. Kroesen, J. Phys. D: Appl. Phys 32 (1999) L133-L137.

(Continued)

*Primary Examiner*—Richard L Chiesa
(74) *Attorney, Agent, or Firm*—Young Basile

(57) ABSTRACT

The present invention provides an air filtration cartridge suitable for use in the treatment of air in a forced airflow air supply system. The cartridge comprises an inner casing having an upstream stage defining a chamber having an inlet for receiving a forced airflow. The chamber has an outlet which leads into a downstream stage comprising a filter holder and mounting a high airflow electrostatic filter. Inside the chamber is a low power coronal discharge ozone generator device.

18 Claims, 2 Drawing Sheets

U.S. PATENT DOCUMENTS

Figure 1:
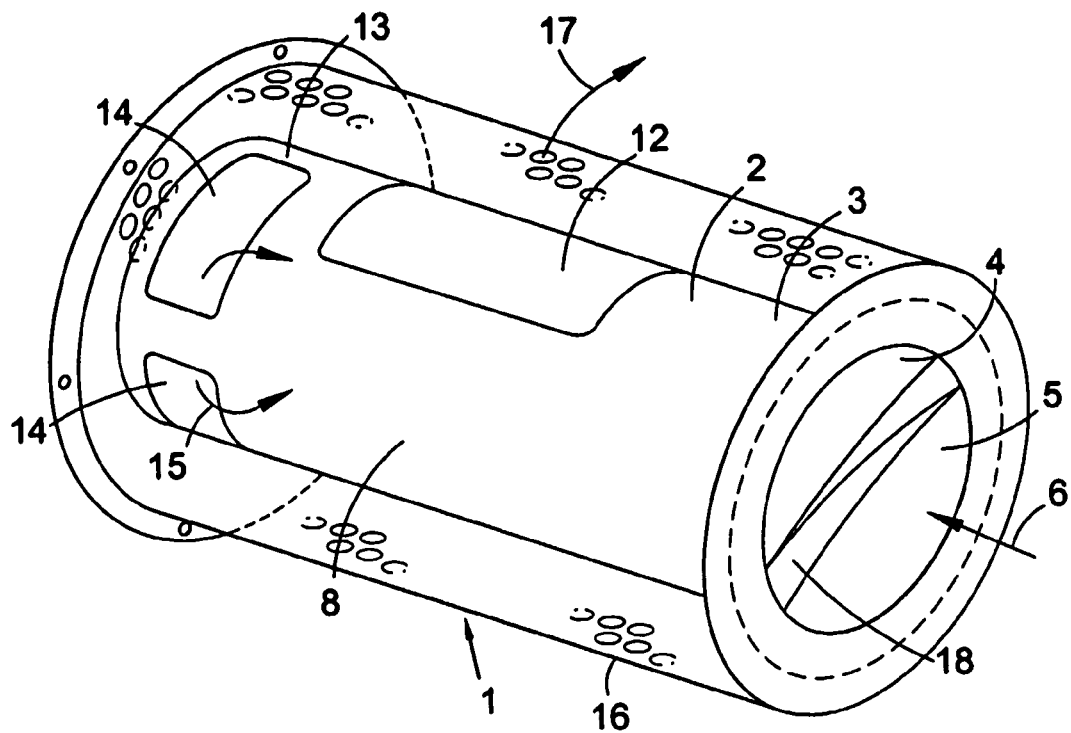

| | | | |
|---|---|---|---|
| 2,841,242 A * | 7/1958 | Hall | 95/58 |
| 2,876,188 A | 3/1959 | Thorp et al. | |
| 2,937,983 A | 5/1960 | Ryan | |
| 3,256,164 A | 6/1966 | Donohue et al. | |
| 3,309,300 A | 3/1967 | Grosse et al. | |
| 3,326,747 A | 6/1967 | Ryan et al. | |
| 3,503,704 A * | 3/1970 | Marks | 423/212 |
| 3,730,874 A | 5/1973 | Trüb | |
| 3,833,492 A | 9/1974 | Bollyky | 204/176 |
| 3,856,671 A | 12/1974 | Lee et al. | 210/63 |
| 3,865,733 A | 2/1975 | Taylor | 250/532 |
| 3,883,413 A | 5/1975 | Douglas-Hamilton | 204/176 |
| 3,892,237 A | 7/1975 | Steiner | 128/216 |
| 3,905,920 A | 9/1975 | Botcharoff | 250/536 |
| 3,921,002 A | 11/1975 | Williams et al. | 250/533 |
| 3,963,625 A | 6/1976 | Lowther | 250/533 |
| 3,967,131 A | 6/1976 | Slipiec et al. | 250/539 |
| 3,988,131 A | 10/1976 | Kanazawa et al. | 55/126 |
| 4,019,986 A | 4/1977 | Burris et al. | 210/139 |
| 4,025,441 A | 5/1977 | Tabata et al. | 250/540 |
| 4,035,657 A | 7/1977 | Carlson | 250/533 |
| 4,048,668 A | 9/1977 | Von Bargen et al. | 361/235 |
| 4,049,400 A | 9/1977 | Bennett et al. | 55/139 |
| 4,049,552 A | 9/1977 | Arff | 210/192 |
| 4,051,045 A | 9/1977 | Yamamoto et al. | 250/536 |
| 4,062,748 A | 12/1977 | Imris | 204/176 |
| 4,079,260 A | 3/1978 | Dmitriev et al. | 250/540 |
| 4,095,115 A | 6/1978 | Orr, Jr. et al. | 250/538 |
| 4,101,783 A | 7/1978 | Hutter | 250/540 |
| 4,123,664 A | 10/1978 | Yamamura et al. | 250/536 |
| 4,124,467 A | 11/1978 | Pincon | 204/157.1 |
| 4,128,768 A | 12/1978 | Yamamoto et al. | 250/535 |
| 4,131,528 A | 12/1978 | Tsujimoto et al. | 204/157.1 |
| 4,140,608 A | 2/1979 | Vaseen | 204/176 |
| 4,159,971 A | 7/1979 | Gneupel | 250/540 |
| 4,167,466 A | 9/1979 | Orr, Jr. et al. | 204/176 |
| 4,167,484 A | 9/1979 | Morikawa | 250/533 |
| 4,182,663 A | 1/1980 | Vaseen | 204/157.1 |
| 4,187,615 A | 2/1980 | Iwata | 34/1 |
| 4,189,363 A | 2/1980 | Beitzel | 204/157.1 |
| 4,202,618 A | 5/1980 | Waschk et al. | 355/3 |
| 4,203,948 A | 5/1980 | Brundbjerg | 422/121 |
| 4,216,096 A | 8/1980 | Parè et al. | 250/539 |
| 4,234,800 A | 11/1980 | Kenly, V et al. | 250/540 |
| 4,244,712 A | 1/1981 | Tongret | 55/124 |
| 4,252,623 A | 2/1981 | Vaseen | 204/157.1 |
| 4,316,782 A | 2/1982 | Foller et al. | 204/129 |
| 4,317,044 A | 2/1982 | Vaseen | 422/186.3 |
| 4,329,212 A | 5/1982 | Obenshain | 204/157.1 |
| 4,351,734 A | 9/1982 | Kauffman | 210/748 |
| 4,370,301 A | 1/1983 | Doi et al. | 422/122 |
| 4,375,395 A | 3/1983 | Foller et al. | 204/129 |
| 4,383,976 A | 5/1983 | Notaro | 422/186.18 |
| 4,386,055 A | 5/1983 | McBride | 422/186.18 |
| 4,411,756 A | 10/1983 | Bennett et al. | 204/176 |
| 4,416,747 A | 11/1983 | Menth et al. | 204/129 |
| 4,417,966 A | 11/1983 | Krauss et al. | 204/176 |
| 4,427,636 A | 1/1984 | Obenshain | 422/186.07 |
| 4,434,771 A | 3/1984 | Slomnicki | 123/539 |
| 4,461,744 A | 7/1984 | Erni et al. | 422/186.18 |
| 4,462,965 A | 7/1984 | Azuma et al. | 422/186.08 |
| 4,504,446 A | 3/1985 | Kunicki et al. | 422/186.19 |
| 4,541,989 A | 9/1985 | Foller | 422/186.07 |
| 4,555,335 A | 11/1985 | Burris | 210/192 |
| 4,614,573 A | 9/1986 | Masuda | 204/176 |
| 4,640,782 A | 2/1987 | Burleson | 210/748 |
| 4,650,573 A | 3/1987 | Nathanson | 210/136 |
| 4,656,010 A | 4/1987 | Leitzke et al. | 422/186.18 |
| 4,690,803 A | 9/1987 | Hirth | 422/186.18 |
| 4,696,800 A | 9/1987 | Sasaki et al. | 422/186.18 |
| 4,725,412 A | 2/1988 | Ito | 422/186.19 |
| 4,764,349 A | 8/1988 | Arff et al. | 422/186.18 |
| 4,786,489 A | 11/1988 | Grenier et al. | 423/581 |
| 4,790,980 A | 12/1988 | Erni et al. | 422/186.15 |
| 4,842,829 A | 6/1989 | Hirai et al. | 422/186.08 |
| 4,857,277 A | 8/1989 | Broomfield | 422/186.07 |
| 4,859,429 A | 8/1989 | Nisenson | 422/186.13 |
| 4,863,497 A | 9/1989 | Grenier et al. | 55/181 |
| 4,877,588 A | 10/1989 | Ditzler et al. | 422/186.19 |
| 4,886,645 A | 12/1989 | Fischer et al. | 422/186.18 |
| 4,904,289 A | 2/1990 | Miyakami et al. | 62/157 |
| 4,909,996 A | 3/1990 | Uys | 422/186.07 |
| 4,941,270 A | 7/1990 | Hoffman | 34/60 |
| 4,960,569 A | 10/1990 | Fovell et al. | 422/186.19 |
| 4,976,920 A | 12/1990 | Jacob | 422/23 |
| 4,981,656 A | 1/1991 | Leitzke | 422/186.18 |
| 4,992,246 A | 2/1991 | Serizawa et al. | 422/186.13 |
| 5,004,587 A | 4/1991 | Tacchi | 422/186.19 |
| 5,008,087 A | 4/1991 | Batchelor | 422/186.22 |
| 5,015,442 A | 5/1991 | Hirai | 422/121 |
| 5,034,032 A | 7/1991 | Yikai et al. | 55/124 |
| 5,034,198 A | 7/1991 | Kaiga et al. | 422/186.07 |
| 5,039,314 A | 8/1991 | Lehner et al. | 55/26 |
| 5,047,127 A | 9/1991 | Tottori et al. | 204/176 |
| 5,055,115 A | 10/1991 | Yikai et al. | 55/124 |
| 5,082,558 A | 1/1992 | Burris | 210/167 |
| 5,093,087 A | 3/1992 | Freeman | 422/186.15 |
| 5,120,512 A | 6/1992 | Masuda | 422/297 |
| 5,124,132 A | 6/1992 | Francis, Jr. et al. | 422/186.07 |
| 5,124,905 A | 6/1992 | Kniepkamp | 363/19 |
| 5,145,653 A | 9/1992 | Fischer et al. | 422/186.18 |
| 5,154,895 A | 10/1992 | Moon | 422/186.07 |
| 5,171,525 A | 12/1992 | Jacob | 562/392 |
| 5,185,903 A | 2/1993 | Choi | 15/339 |
| 5,186,903 A | 2/1993 | Cornwell | 422/122 |
| 5,203,972 A | 4/1993 | Shimamune et al. | 204/129 |
| 5,207,993 A | 5/1993 | Burris | 422/256 |
| 5,213,773 A | 5/1993 | Burris | 422/256 |
| 5,221,520 A | 6/1993 | Cornwell | 422/122 |
| 5,223,105 A | 6/1993 | Arthurson | 204/176 |
| 5,230,220 A | 7/1993 | Kang et al. | 62/78 |
| 5,268,151 A | 12/1993 | Reed et al. | 422/186.16 |
| 5,302,343 A | 4/1994 | Jacob | 422/23 |
| 5,306,471 A | 4/1994 | Harbert et al. | 422/186.18 |
| 5,332,563 A | 7/1994 | Chang | 423/245 |
| 5,366,703 A | 11/1994 | Liechti et al. | 422/186.11 |
| 5,368,816 A | 11/1994 | Detzer | 422/28 |
| 5,387,400 A | 2/1995 | Pelster | 422/186.03 |
| 5,411,713 A | 5/1995 | Iwanaga | 422/186.15 |
| 5,445,798 A | 8/1995 | Ikeda et al. | 422/121 |
| 5,460,705 A | 10/1995 | Murphy et al. | 204/252 |
| 5,466,425 A | 11/1995 | Adams | 422/186.3 |
| 5,478,533 A | 12/1995 | Inculet | 422/186.07 |
| 5,484,472 A | 1/1996 | Weinberg | 96/26 |
| 5,484,570 A | 1/1996 | Ikeda et al. | 422/1 |
| 5,493,754 A | 2/1996 | gurstein et al. | 15/321 |
| 5,520,893 A | 5/1996 | Kasting, Jr. et al. | 422/305 |
| 5,527,459 A | 6/1996 | Ikeda et al. | 210/188 |
| 5,529,760 A | 6/1996 | Burris | 422/186.07 |
| 5,593,598 A | 1/1997 | McGinness et al. | 210/748 |
| 5,601,786 A | 2/1997 | Monagan | 422/108 |
| 5,611,868 A | 3/1997 | Gurstein et al. | 134/21 |
| 5,656,063 A | 8/1997 | Hsu | 95/58 |
| 5,656,242 A | 8/1997 | Morrow et al. | 422/121 |
| 5,667,563 A * | 9/1997 | Silva, Jr. | 96/50 |
| 5,667,564 A | 9/1997 | Weinberg | 96/58 |
| 5,681,533 A | 10/1997 | Hiromi | 422/121 |
| 5,702,507 A | 12/1997 | Wang | 96/55 |
| 5,752,878 A | 5/1998 | Balkany | 484/236 |
| 5,759,487 A | 6/1998 | Jung | 422/22 |
| 5,766,560 A | 6/1998 | Cole | 422/186.18 |
| 5,814,135 A | 9/1998 | Weinberg | 96/58 |
| 5,820,828 A | 10/1998 | Ferone | 422/124 |
| 5,824,274 A | 10/1998 | Long | 422/186.07 |

| | | | | |
|---|---|---|---|---|
| 5,833,740 A | 11/1998 | Brais ............................ 96/16 |
| 5,872,426 A | 2/1999 | Kunhardt et al. ............ 313/582 |
| 5,880,916 A | 3/1999 | Hsieh .......................... 361/230 |
| 5,904,896 A | 5/1999 | High ............................. 422/4 |
| 5,939,030 A | 8/1999 | Moxley et al. .......... 422/186.07 |
| 5,961,919 A | 10/1999 | Tachibana et al. ............... 422/3 |
| 5,972,196 A | 10/1999 | Murphy et al. ............... 205/466 |
| 6,005,349 A | 12/1999 | Kunhardt et al. ......... 315/111.21 |
| 6,013,021 A | 1/2000 | Lee ................................ 600/9 |
| 6,013,189 A | 1/2000 | Burris .......................... 210/750 |
| 6,039,884 A | 3/2000 | Burris et al. ................. 210/760 |
| 6,042,637 A | 3/2000 | Weinberg ........................ 96/58 |
| 6,147,452 A | 11/2000 | Kunhardt et al. ............. 313/582 |
| 6,153,151 A | 11/2000 | Moxley et al. .......... 422/186.07 |
| 6,176,977 B1* | 1/2001 | Taylor et al. ................. 204/176 |
| 6,200,539 B1 | 3/2001 | Sherman et al. ......... 422/186.04 |
| 6,277,291 B1 | 8/2001 | Burris .......................... 210/760 |
| 6,342,187 B1 | 1/2002 | Jacob et al. ............. 422/186.05 |
| 6,375,904 B1 | 4/2002 | Skillman et al. ............. 422/172 |
| 6,387,241 B1 | 5/2002 | Murphy et al. ............... 205/626 |
| 6,391,269 B1 | 5/2002 | Yoshimatu ............. 422/186.07 |
| 6,447,731 B1 | 9/2002 | Sun et al. .................... 422/121 |
| 6,468,953 B1 | 10/2002 | Hitchems et al. ............ 510/218 |
| 6,475,215 B1 | 11/2002 | Tanrisever ................... 606/45 |
| 6,503,458 B1 | 1/2003 | Ogle .......................... 422/121 |
| 6,508,982 B1 | 1/2003 | Shoji ............................ 422/22 |
| 6,545,608 B1 | 4/2003 | Kaufman .................... 340/577 |
| RE38,130 E | 6/2003 | Adams .................... 422/186.3 |
| 6,589,486 B1 | 7/2003 | Spanton ...................... 422/121 |
| 6,589,489 B2 | 7/2003 | Morrow et al. ........... 422/186.3 |
| 6,673,137 B1 | 1/2004 | Wen ............................ 96/224 |
| 6,680,028 B1 | 1/2004 | Harris ........................ 422/122 |
| 2002/0039577 A1 | 4/2002 | Townsend et al. |
| 2002/0058000 A1 | 5/2002 | Smith |
| 2002/0094309 A1 | 7/2002 | Burris et al. |
| 2002/0098109 A1 | 7/2002 | Nelson et al. |
| 2002/0134736 A1 | 9/2002 | Burris et al. |
| 2003/0113246 A1 | 6/2003 | Saitou et al. |
| 2003/0146082 A1 | 8/2003 | Gibson et al. |
| 2004/0047776 A1 | 3/2004 | Thomsen |

FOREIGN PATENT DOCUMENTS

| | | |
|---|---|---|
| CH | 669 116 A5 | 2/1989 |
| DE | 195 13 943 A1 | 10/1996 |
| DE | 298 08 126 U1 | 9/1998 |
| DE | 199 36 455 A1 | 2/2001 |
| DE | 199 42 839 A1 | 4/2001 |
| DE | 100 14 485 A1 | 9/2001 |
| EP | 0 731 320 A2 | 9/1996 |
| EP | 0 824 041 A2 | 2/1998 |
| EP | 1 079 183 A2 | 2/2001 |
| EP | 1 175 943 | 1/2002 |
| EP | 1 249 265 A1 | 10/2002 |
| EP | 1 348 448 A1 | 10/2003 |
| FR | 2 835 517 | 8/2003 |
| GB | 1 531 309 | 11/1978 |
| GB | 2 229 365 A | 3/1990 |
| GB | 2 340 035 A | 7/1998 |
| GB | 9916349.5 | 11/1999 |
| GB | 2 358 350 A | 7/2001 |
| JP | 62057662 A | 3/1987 |
| JP | 11-56673 | 6/1989 |
| JP | 03035018 A | 2/1991 |
| JP | 03207363 A | 9/1991 |
| JP | 05044958 A | 2/1993 |
| JP | 06105897 A | 4/1994 |
| JP | 07232028 A | 9/1995 |
| JP | 08114332 A | 5/1996 |
| JP | 08173517 A | 7/1996 |
| JP | 08253025 A | 10/1996 |
| JP | 09075436 A | 3/1997 |
| JP | 10253096 A | 9/1998 |
| JP | 200140688 A | 5/2000 |
| JP | 2000153178 A | 6/2000 |
| JP | 2001046906 | 2/2001 |
| JP | 2002276999 A | 9/2002 |
| RU | 19894708691 | 5/1998 |
| WO | WO 97/34682 | 9/1997 |
| WO | WO 00/01737 | 1/2000 |
| WO | 02/25180 A1 | 3/2002 |
| WO | WO 03/028773 A1 | 4/2003 |
| WO | WO 2004/047877 A2 | 6/2004 |

OTHER PUBLICATIONS

*Cold Plasma Reactor with Dielectric Barrier Discharge*, printed by T. Opalinska, printed by Industrial Chemistry Research Institute, Rydygiera 8, 01 792 Warszawa, Poland.

*A Compact Corona Discharge Device (CDD™) for Non-Thermal Plasma Generation in Gasoline or Diesel Engine Exhaust*, Jack Ekchian, Vic Nowak, and Jim Rush, printed by Litex, Inc.

*Effects on Bacteria and Viruses*, written by Ozonet—Warren Wood, from website of Ozone Solutions, Inc.

*Make Some Ozone*, article taken from http://www.emanator.demon.co.uk/bigclive/ozone.html website.

*Honeywell Electronic Air Cleaners*, advertisement taken from http://www.hvacoracle.com/parts/ventilation/hw_eac.html website on Jul. 7, 2004.

QuickPure™ by Alab, LLC advertisement taken from http://www.quickpure.com/pg0.html website on Jun. 3, 2003.

ARIA PureAir Ltd. advertisement *Produce Comparisons*, taken from http://www.ariaair.com/comp.asp website on Feb. 7, 2003.

*Ozone Generators that are Sold as Air Cleaners: An Assessment of Effectiveness and Health Consequences, Indoor Air*—Publications article by U.S. Environmental Protection Agency.

*Investigation of gaseous ozone for MRSA decontamination of hospital side-rooms*, A. W. Berrington and S. J. Pedler, article by NCBI Pub Med 1: J Hosp Infect. Sep. 1998; 40(1):61-5; (National Library of Medicine "NLM") from NCBI website.

*Ozone Disinfection* Fact Sheet, by Clement Solomon, Peter Casey, Colleen Mackne, & Andrew Lake, project funded by the U.S. Environmental Protection Agency under Assistance Agreement No. CX824652; Technology Initiative (ETI), © 1998 by the National Small Flows Clearinghouse.

*Fundamentals of Ozonation* by Ron Brook and Ron Barnes (of Prozone Internation, Inc.), Home Vistek Commercial Ozone Systems.

Ozone Air disinfection and deodoursation advertisement for ozone generator taken from website http://www.1x1x1.com/ozone/air_disinfection.

*Biozone® PureWave™ versus Corona Discharge* article by Biozone Scientific advertisement from http://www.inspiredliving.com/cleanair/compare_coronadischarge.html website.

*Overview of Ozone*, article from ARCE Systems, Inc. website: info@arcestems.com.

*Ozone Generation in Dry Air Using Pulsed Discharges with and without a Solid Dielectric Layer*, article by W. J. M. Samaranayake, YT. Miyahara, T. Namihira, S. Katsuki, R. Hackam, H. Akiyama, published: IEEE Trans. DEI, vol. 87 pp. 687-697, 2001.

*Corona Discharge Treatment for Medical Surface Preparation*, by Bruce Stobbe, article from Medical Device & Diagnostic Industry Magazine, originally published Feb. 2000, from website: http://www.devicelink.com/mddi/archive/00/02/004.html.

*A Simple and Efficient Ozone Generator* by Debra J. Sponholtz, Michael A. Walters, Jimmy Tung, and Joseph J. BelBruno, *Journal of Chemical Education*, vol. 76, No. 12, Dec. 1999, Department of Chemistry, Dartmouth College, Hanover, NH 03755.

*A History of Patented Methods of Ozone Production From 1897 to 1997*, IAngela E. Miller, Wm. R. Grow, Leigh Ann Dees, Michael R. Mitchell, Thomas J. Manning, Laboratory of Physical Environmental Sciences Department of Chemistry, Valdosta State University, Valdosta, GA 31698.

*Electrical Discharges (How the spark, glow and arc work)*, article composed by J. B. Calvert, Nov. 3, 2002, on website http://www.du.edu/~jcalvert/phys/dischg.html.

*The Fontan Device*, article taken from website http://cloudbase.phy.umist.ac.uk/people/dorsey/Font.html on Jul. 3, 2003.

*5.2 Ozonolysis of Alkenes under Atmospheric Conditions*, article taken from website http://www.physchem.uni-suppertal.de/P.../05_2_Ozonolysis/05_2_1_Peroxides.html on Jul. 3, 2003.

*3. Ozone*, EPA Guidance Manual, "Alternative Disinfectants and Oxidants", Apr. 1999.

*Ozone Out for Indoor Air Cleaners*, by John Manuel, from "Home Energy Magazine Online" Nov./Dec. 1998, from website http://hem.dis.anl.gov/eehem/98/981110.htrl.

*The Technical Merits and Application of Different Types of Air Cleaning Technology*, by Stephen H. Zitin of Bioclimatic, Inc., May 13, 2003, from website: http://www.wescorhvac.com/BioPaper.html.

*Frequently Asked Questions About our IG-133- model series ionizers*, from advertisement of copyright © 2004 Comtech Research LLC, Dec. 16, 2004.

*The Low Voltage Ozone Generator*, Sergey I. Andreev, by Ohio Scientific Consulting Corporation, (OSCC).

* cited by examiner

AIR FILTRATION DEVICE

CROSS-REFERENCE TO RELATED APPLICATIONS

This application is the national stage of International Application No. PCT/GB04/03140, filed on Jul. 19, 2004, which claims benefit of U.S. Provisional Application No. 60/577,952 filed on Jun. 8, 2004 and foreign applications GB 0316837.4 filed Jul. 18, 2003, GB 0409547.7 filed Apr. 29, 2004, and GB 0410648.0 filed May 13, 2004.

FIELD OF THE INVENTION

The present invention relates to an apparatus and method for the removal of airborne pollutants or impurities such as micro-organisms, smoke particles or odours from air by means of transient treatment of the air in a low power corona discharge field, in forced air-flow air-conditioning systems, especially in situations such as aircraft and submarines etc where the air is recirculated many times.

BACKGROUND OF THE INVENTION

The use of ozone in many applications involving sterilising and cleaning air is well known. Ozone generating devices have been designed for a great variety of domestic and industrial applications. All depend on ozone's great oxidising potential to kill micro-organisms and oxidise other organic particles and materials. Depending on the application, ozone is generated by means of ultraviolet radiation or electrical discharge to convert atmospheric oxygen to triatomic ozone, which can be highly effective at destroying organic atmospheric contaminants. Ozone is, however, highly toxic at high concentrations and it is increasingly clear that even at much lower concentrations it is irritant, being particularly linked with asthmatic complaints in those chronically exposed to it. In many territories there are strict statutory limits on the concentration of ozone to which members of the public and employees at a place of work may be exposed. In the UK, the Health and Safety Executive recommendation (EH38) is that the exposure limit to ozone should be 0.1 ppm (0.2 mg m$^{-3}$) as an 8-hour time-weighted average concentration, with a short-term exposure limit of 0.3 ppm (0.6 mg m$^{-3}$) as a 15-minute time-weighted average concentration.

Although undoubtedly effective at high concentrations, there is considerable evidence that ozone is ineffective as a biocide or in oxidising organic contaminants at concentrations that are safe for chronic human exposure (Dyas et al, 1983, J Clin Pathol 36: 1102-1104; Berrington and Pedlar, 1998, J Hosp Infect 40: 61-65; Esswein et al, 1994, Appl Occup Environ Hygiene 9: 139-146). Such effect as it has in reducing odours is, in many cases, probably a mere masking with its own characteristic smell.

Alternative approaches to removing micro-organisms and other small airborne organic particles, such as smoke, obviously include direct filtration of the air. Various type of filter including so-called High Efficiency Particulate Air (HEPA) filters (defined as removing 99.97% of particles of 0.3 micron size) and electrostatic HAF (High Airflow, electret) filters capable of similar performance at higher airflows are commonly used. Although effective in some situations, such filters suffer from the disadvantages that trapped (and potentially infective) material remains on the filters, necessitating frequent changes of filter and remaining a hazard until the filters are replaced. This is a particular problem where the air being filtered is humid. In addition, such filters are incapable of removing small viral particles.

In addition to the abovementioned problems, conventional filtration systems used in aircraft air supply systems in which cabin air is repeatedly recycled with a small proportion thereof being replaced by fresh air from outside the aircraft, present particular problems, due to the extreme temperature ranges encountered. Usually such filtration systems employ HEPA filters mounted in mesh cages. One significant limitation of HEPA filters is the relatively low face speed thereof, i.e. the maximum airflow speed across the face of the filter at which particles of a given size can be trapped by the filter. The filter material frequently becomes damp which significantly increases the resistance to the airflow, thereby substantially increasing the load on the air circulation drive, which in turn substantially increases the fuel consumption of the aircraft. This problem is even further aggravated by freezing of the damp filter material at the very low temperatures encountered at typical airliner cruising altitudes. A further consequence of such freezing is that it can result in buckling and distortion of the mesh cage which in turn often results in jamming of the filter cartridge inside the cartridge mounting thereby increasing maintenance downtime and cost.

In my earlier GB 2358350 there is disclosed a proposed hand drier apparatus using a corona unit with quartz glass and stainless steel mesh electrodes and operating at 9 mA and 4 kv in order to eject a stream of ozone at the user. Further research has disclosed, however, that the proposal as disclosed in this publication would be quite impractical—quite apart from exposing the user to dangerous levels of ozone.

Thus there remains a need for an efficient means of removing airborne pollutants such as organic particles, micro-organisms and odours from air in forced airflow circulation systems, without release of potentially hazardous levels of ozone into an enclosed environment, and whilst minimizing air flow resistance.

SUMMARY OF THE INVENTION

The current invention concerns a method of using a low power corona discharge field to effectively sterilise air of micro-organisms or oxidise organic airborne contaminants and particles in such a way that the air is only transiently exposed to high concentrations of ozone and is returned to the environment with the level of ozone reduced to acceptable levels for safe exposure of those living or working in the immediate environment, and trapping particles in the air treated by the ozone generator, in a low resistance high airflow electrostatic filter. Preferably the concentration of ozone expelled after treatment is less than 0.3 ppm. Preferably, it is less than 0.2 ppm and more preferably less than 0.1 ppm.

It has now been found that it is possible, using a low power coronal discharge ozone generator unit, to generate restricted ozone concentrations within an inactivating zone in close proximity to the unit and contained within the apparatus housing, which are sufficient to inactivate a wide range of airborne pollutants in an airflow passing through said zone, yet which reduce to safe levels sufficiently rapidly that the treated air issuing from the apparatus has physiologically acceptable ozone concentrations without the need for special catalyzers. Extensive experimental work (discussed in detail hereinbelow), has shown that even with ozone concentrations up to 100 ppm in the inactivation zone, exit concentrations of less than 0.1 ppm are achieved.

Thus in one aspect the present invention provides an air filtration cartridge suitable for use in the treatment of air in a forced airflow air supply system having an air supply conduit provided with an in-line filtration cartridge mounting formed and arranged for releasably mounting a replaceable air filtration cartridge so that the air supply is passed through said cartridge, said cartridge comprising a casing having: an upstream stage defining a chamber having an inlet for receiving a said forced airflow, in use of the cartridge, and an outlet, and mounting, inside said chamber, at least one low power coronal discharge ozone generator, said at least one ozone generator being formed and arranged for generating a restricted concentration of ozone and any other reactive species formed together therewith, within an inactivating zone contained within said cartridge, through which said air flow is passed in use of said cartridge, which restricted concentration is sufficient effectively to inactivate airborne pollutant material entrained in said air flow, yet which restricted concentration decays sufficiently outside said inactivating zone so that the concentration of ozone in the cleaned air expelled from said cartridge, is at a physiologically acceptable level; and a downstream stage coupled to said upstream stage outlet and formed and arranged for mounting, in use of the cartridge, a high airflow electrostatic filter.

As used herein the expression "inactivating zone" means a restricted volume surrounding the low power corona discharge ozone generator containing an elevated concentration of ozone (and any other reactive species may be generated together with the ozone by the low power coronal discharge ozone generator), sufficient to substantially inactivate airborne pollutants.

In accordance with the present invention the low power coronal discharge ozone generator is formed and arranged so that the inactivating zone is contained within the cartridge, preferably within the chamber, i.e. does not extend outside of the confines thereof. The cartridge casing defining the chamber may be any convenient form but typically is cylindrical. The chamber is provided with (at least one) inlet and (at least one) outlet, of any convenient form, for example a conduit or simply one or more apertures capable of passing the forced airflow through the inactivating zone of the apparatus and out though the outlet(s) into the filter.

Advantageously the inlet portion of the chamber is provided with an airflow diverter formed and arranged to impart a twist to the flow of air through the chamber resulting in an increased residence time in the inactivation zone and a somewhat turbulent flow around the ozone generator(s) through the chamber and the inactivating zone.

I have found that the ozone generators are substantially effective in inactivation of a wide range of airborne pollutants at a wide range of air flow rates. In practice the cartridge parameters will normally be adapted to the requirements of the air supply system and the flow rate thereof. In particular the number of ozone generators and disposition thereof will generally be chosen so as to ensure that the inactivation zone(s) of the ozone generator(s) extend substantially across the whole of the airflow path through the upstream stage of the cartridge.

Similarly I have found that effective inactivation and ozone containment within the cartridge, may be achieved with a relatively wide range of residence times of the airflow within the chamber of the cartridge. Preferably there is used a residence time in the range from 0.2 to 20 seconds, preferably from 0.3 to 15 seconds, advantageously from 0.5 to 10 seconds.

In addition to the particular benefit of providing a rapidly decaying restricted concentration ozone supply, such low power coronal discharge ozone generators also have significant safety benefits in the case of any possible apparatus malfunctions, maintenance operations etc. Power to provide a suitable ozone-generating corona discharge is suitably provided by a transformer providing a high-voltage alternating current. It will be appreciated that the voltage and current parameters of the unit required to achieve a corona discharge will depend principally on the nature of the dielectric used, as further discussed hereinbelow. In general though I have found that operating voltages below 1 kV are not practical, and preferably there is used an operating voltage in the range from 1 to 6 kV, most desirably from 3 to 5 kV, for example about 4 kV. It will be appreciated that the current required to maintain the corona discharge is significantly less than that required to initiate it. The current (and hence power) of coronal discharge ozone generator units is normally expressed in terms of the starting current. In general I have found that there should be used a (starting) current in the range from 1 to 10 mA, preferably at least 3 mA. The power of the unit will of course depend on the voltage and current combination. Restriction of the power of the unit helps to ensure that the inactivation field is contained within the chamber. In this connection it will be appreciated that a somewhat higher power unit might, in principle, be used with a larger chamber. The power should generally be not more than 50 watts, and is preferably at least 4 watts. Typically the power is in the range from 10 to 40 watts. These power levels have in particular been found to be convenient with a unit having a chamber volume of the order of 0.02 to 1.0 $m^3$. (It will be appreciated that on the one hand the chamber should not be smaller than a volume required to contain said inactivation zone of the ozone generator(s), and on the other hand not so large that the whole of the airflow does not pass through said inactivation zone in the course of its transit through the chamber.)

Even with such low power corona discharge devices it has been found possible to achieve well contained localized highly inactivating concentrations of ozone sufficient to inactivate a very wide range of airborne pollutants.

Advantageously there is used a transformer provided with an anti-surge and/or anti-spike device(s), in order to minimize transient excursions of the output voltage above the normal level which could result in temporary extension of the inactivation zone outside of the chamber and/or generation of excessively high ozone levels.

Desirably also there is used a transformer which is "potted" or encased in a suitable insulating material in order to minimize the risk of possible breakdown in the course of use of the cartridge of the invention.

A wide range of frequencies may be used in the AC supply to the low power corona discharge device, and indeed somewhat higher frequencies may safely be used than is possible with conventional high power ozone generators. Conveniently there may be used an AC supply with a frequency in the range from 50 to 1000 Hz, for example, around 400 Hz as is commonly found in power supplies available on aircraft.

Various forms of low power corona discharge device are known in the art. In accordance with the present invention there is desirably used one with a solid dielectric in order to obtain a more consistent and reliable ozone generation performance. Various geometries are also possible. Thus, for example, there may be used a substantially planar unit with a flat dielectric plate with electrodes on opposite sides thereof. More preferably there is used a generally tubular geometry, with a tubular dielectric with generally tubular electrodes on the inner and outer faces thereof. It will be appreciated that ozone will be generated at both electrodes. Preferably there is used a generally mesh form electrode in order to maximize the areas of dielectric surface at which ozone is generated. In this connection it will be appreciated that substantially "closed" meshes are less desirable as these reduce the exposed dielectric surface. On the other hand excessively "open" meshes are generally less efficient in the amount of ozone generated for a give size of unit.

In a highly preferred embodiment, the low power corona discharge ozone generator comprises tubular stainless steel gauze electrodes separated by a silica glass dielectric. (Whilst various other suitable electrode materials are known in the art, stainless steel is particularly convenient due to inter alia its resistance to corrosion and to oxidative and other damage from the corona discharge.) The purpose of gauze electrodes is to maximize the surface available for the corona discharge and hence generation of ozone and other reactive species. However, other factors, such as the effects on the electromagnetic field generated, particularly hysteresis effects relating to the generation and collapse of the field during the 50 Hz cycle of the alternating current, also influence the choice of gauze and the fineness of the mesh. In a preferred embodiment the gauze on the outer electrode is coarser than that of the inner electrode as this favours the production of ozone on the outer, rather than inner, electrode. In a more preferred embodiment, the mesh count of the inner electrode is from 50 to 30×45 to 25 (per inch or 25.4 mm) and that of the outer electrode is 35 to 20×40 to 20. In a particularly favoured embodiment, the mesh count of the inner electrode is 40×34 (per inch or 25.4 mm) using a 38 swg wire (0.15 mim diameter) and that of the outer electrode is 24×28 using a 30 swg wire (0.3 mm diameter).

It is also desirable for effective corona discharge to take place that the mass of the electrodes be substantially balanced, i.e. to differ by not more than 20%, preferably not more than 10%. This is especially significant in the case of annular configuration corona discharge devices of the kind described elsewhere herein.

It will also be appreciated that the power of the corona discharge ozone generator is related to the size of the electrodes. In general it is preferred that each of the mesh electrodes should have an area in the range from 25 to 100 $cm^2$, preferably from 40 to 90 $cm^2$.

It will be appreciated that with a solid dielectric, the generation of a corona discharge is very much dependent on the thickness of the dielectric, and especially at lower voltages, as used in accordance with the present invention, it is necessary to minimize the thickness of the dielectric. It will also be understood, though, that the dielectric must be strong enough to avoid damage by the substantial stresses encountered inside a corona discharge. In this connection I have found that conventional glasses when used at thicknesses low enough for corona discharge to occur at voltages used in accordance with the present invention are highly susceptible to shattering, and it is necessary to use suitably strengthened glasses. Suitable glasses include borosilicate glass, especially borosilicate glass strengthened with titanium dioxide. Preferably there is used a glass dielectric having a wall thickness of from approximately 0.70 mm to 1.75 mm, and more preferably from 0.8 to 1.1 mm, in order to withstand the stresses of the discharges and to have suitable dielectric qualities to allow a corona discharge to take place. It is also advantageous if the glass is a high quality quartz silicate or borosilicate with added titanium dioxide.

Ozone generation occurs during the negative half cycle of the alternating current, at each electrode in turn. During the corresponding positive half cycle there is a tendency for resident ozone to be broken down, but this is a slower process than generation, and in any case the flow of air removes ozone from the corona discharge area as it is formed. This leads to a net production of ozone. The electrochemistry of such methods of ozone production is known in the art.

Ozone thus generated spontaneously breaks down. The half-life in air is dependent on a variety of factors including temperature and concentration but is generally at least several minutes or hours. However, this half-life is generally significantly shortened by humidity and by the presence of oxidisable substrates, solid surfaces and specific catalysts. The generation of ozone in accordance with the present invention in a restricted inactivation zone around a low power corona discharge ozone generator unit, in such a way that it rapidly decomposes to a physiologically acceptable level outside the zone, which obviates the need for the use of special catalysts, is conveniently referred to by the applicant as "closed coupled-field" generation technology.

It should be noted that, although corona discharge is a convenient method of generating ozone, a number of other highly reactive oxygen and nitrogen species may also be generated in air alongside the ozone. The presence of these excited molecules and the generation of further reactive products by their inter-reactions can further contribute to the inactivating activity in the inactivation zone surrounding the alternating current corona discharge tube of the invention.

The inactivating effect of the cartridge of the invention may be used for inactivating a wide range of pollutants, including inter alia microbiological pollutants such as airborne bacteria, viruses and fungal spores, smoke, and various volatile organic compounds, in a wide range of situations so as to improve the quality of the air.

In situations where the cartridge is also required to remove smoke particles, it is preferred that the burden of oily and tarry particulates especially particles passing into the inactivation zone is reduced by the presence of a pre-filter upstream of the inactivation zone, conveniently at the inlet to the upstream stage chamber of the cartridge. Various filters suitable for trapping such pollutants are well known in the art.

Electrostatic filters are well-known in the art. In principle, they use charged filter media to trap charged particles. Most small units are passive in that they use the friction due to the passage of air through the filter to generate a static charge on specialised materials, which is the principle of the well-known HEPA filters. More recently, permanently polarised 'electret' filter media with particularly high electrostatic charge surfaces, as described in (Myers & Arnold, Winter 2003, International Nonwovens Journal and International patent application publication WO 00/01737), have formed the basis of so-called HAF (High Air-Flow) filters, which have far greater face speeds whilst maintaining highly efficient filtering of very small particles (down to 0.1μ) are especially suitable for use in cartridges of the present invention. Large industrial electrostatic precipitators (or 'electronic' filters) use charged plates or a corona discharge to actively impart charge to airborne particles. As used herein, 'electrostatic filters' includes all of these types.

The cartridge filter mounting may have any convenient geometry but typically will be cylindrical. The cross-sectional area and depth thereof will generally be determined by inter alia the airflow requirements of the air supply system and by the desired replacement cycle period for the filter, which in turn will depend on factors such as the average airborne pollutant loadings and the efficiency of the filter. Typically there would be used a filter mounting with a cross-sectional area of from 100 to 2500 $cm^2$, conveniently from 300 to 1500 $cm^2$, albeit in principle there is no upper limit. The filter mounting preferably has a depth of the order of from 5 to 50 cms. The filter may be in the form of a single element, or more conveniently may be in the form of a stack of filter elements. In the latter case the filter passages of the elements are preferably substantially aligned with each other, albeit with the relatively open form of structure used in the preferred type of high airflow Filtrete™ electrostatic filters used in accordance with the present invention, this is not especially critical.

Another particular benefit of the present invention that may be mentioned, is the substantially reduced back pressure produced by the cartridge in use thereof, thereby reducing aircraft fuel consumption etc, whilst maintaining or significantly improving filtration performance as compared with conventional systems. This may moreover be reduced still further in a preferred form of the invention in which the downstream stage includes an annular air reservoir extending around the filter housing, downstream of said filter whereby the flow of air back into the aircraft recirculation system is unrestricted.

Without being bound by any particular theory or model, it is possible that the combination of the ozone generating low power corona discharge ozone generator unit of the invention, combined with an electrostatic post-filter, may provide a particular synergistic benefit with the filter materials, which in some way increases the electrostatic attraction between the airborne particulates emerging from the inactivation zone and the filter surfaces, which results in a significant reduction in the size of the particles which may be trapped by the electrostatic filter used in preferred forms of cartridge of the invention, which has been found by the inventor. This is particularly significant in relation to viruses as these generally have a size of the order of 0.1 micron, which is below the normal minimum particle size of 0.3 microns which can be trapped by HAF filters. Examination of HAF filters used in cartridge of the present invention indicates though that even such viral particles can be successfully trapped, as well as being inactivated.

In accordance with the present invention the concentration of ozone in the air expelled from the cartridge is at a physiologically acceptable level. In practice different countries have slightly higher or lower standards for what are considered to be acceptable levels. In general it is preferred that the air expelled from the cartridge should have an ozone concentration of less than 0.3 ppm at 1 meter from the cartridge air exhaust outlet, more preferably less than 0.2 ppm, most preferably less than 0.1 ppm. Desirably the ozone concentrations are less than these values at the exhaust outlet. An important consideration is the accumulation of ozone in the area supplied by the air supply system during operation. Preferably the concentration of ozone at 1 meter from the air supply outlet after 15 minutes of operation is less than 0.3 ppm, more preferably less than 0.2 ppm, most preferably less than 0.1 ppm.

The chamber of the cartridge is generally defined by a casing which may be of any convenient material. Advantageously the casing is comprised of metal, for example steel or aluminum, or a plastics material (or GRP) impregnated and/or coated with metallic material, suitable to suppress radio frequency interference resulting from the corona discharge and is suitably earthed.

It will be appreciated that a particular benefit of the invention is in increasing the usefulness of filters, particularly filters designed to remove airborne micro-organisms. In many conventional air filters wherein micro-organisms which have not previously been inactivated, are trapped, these tend to multiply more or less rapidly thereby presenting a hazard in handling of the filter when it is replaced, and increasing the risk of release of active micro-organisms back into the airflow emerging from the filter. With a cartridge of the present invention, however, the micro-organisms are substantially inactivated prior to being trapped by the filter, thereby avoiding the above disadvantages. Any which have been trapped without having been fully inactivated, may moreover be subjected to further inactivation treatment by any residual ozone passing into the filter. In this way, the combination of highly efficient filters, such as HEPA or HAF electrostatic filters capable of effectively removing particles as small as 0.1 to 0.3 microns, may provide a further synergistic effect, with an increased benefit over that obtained over either alone, in terms of prolonged efficient filtering and killing of potentially infective micro-organisms.

Another particularly useful benefit of the cartridge of the invention is one wherein air needs to be cleaned of smoke particles. In this case the inlet(s) is fitted with one or more filters. Preferably, the filter assembly comprises two or more filter elements, more preferably, at least one of the elements is an electrostatic filter. In the case of applications where the smoke comprises tobacco smoke, there is advantageously used a filter element which traps oil and/or tar materials found in such smoke.

In another aspect the present invention provides a method of cleaning air without the use of an ozone decomposition catalyzer, comprising the steps of:

providing a cartridge as described above with a said high airflow electrostatic filter mounted in the filter mounting thereof;

powering the ozone generator of said cartridge so as to generate ozone in the inactivation zone of said cartridge; and passing a flow of said air through said inactivation zone and then though said filter.

It will be appreciated that in general where airborne pollutants are being removed from an aircraft cabin or other similar space, the amount of treatment required will depend on the nature of the pollutant, and possibly also the burden or loading thereof in the air. Whilst there may in principle be used multiple passes to progressively reduce the pollutant loading, it is a particular advantage of the invention that the relatively high ozone concentrations which can be achieved with cartridge of the invention within the restricted contained inactivation zone, can usually provide substantially complete inactivation within a single pass, thereby minimizing the number of air changes required and avoiding the risk of cross-infaction amongst passengers. Typically where it is desired to remove bacterial pollutants there should be provided at least 5 air changes per hour, whilst in the case of locations with moderate to high tobacco smoke loadings, it may be desirable to provide at least 10 or more air changes. The total airflow required to treat an aircraft cabin may be readily determined from the volume of the room and the number of air changes required.

DETAILED DESCRIPTION OF THE INVENTION

Further preferred features and advantages of the invention will appear from the following detailed examples and description given by way of example with reference to the accompanying drawings in which:

FIG. 1 shows a general perspective view of a first embodiment of an air treatment cartridge of the invention suitable for the removal of micro-organisms from air;

FIG. 2 is a longitudinal section through the cartridge of FIG. 1;

FIG. 3 is a transverse section through the cartridge of FIG. 1; and

FIG. 4 shows the construction of one of the corona discharge units of the cartridge of FIG. 1.

EXAMPLE 1

Cartridge for use in an Aircraft Air Supply System

Construction

Figure 2:
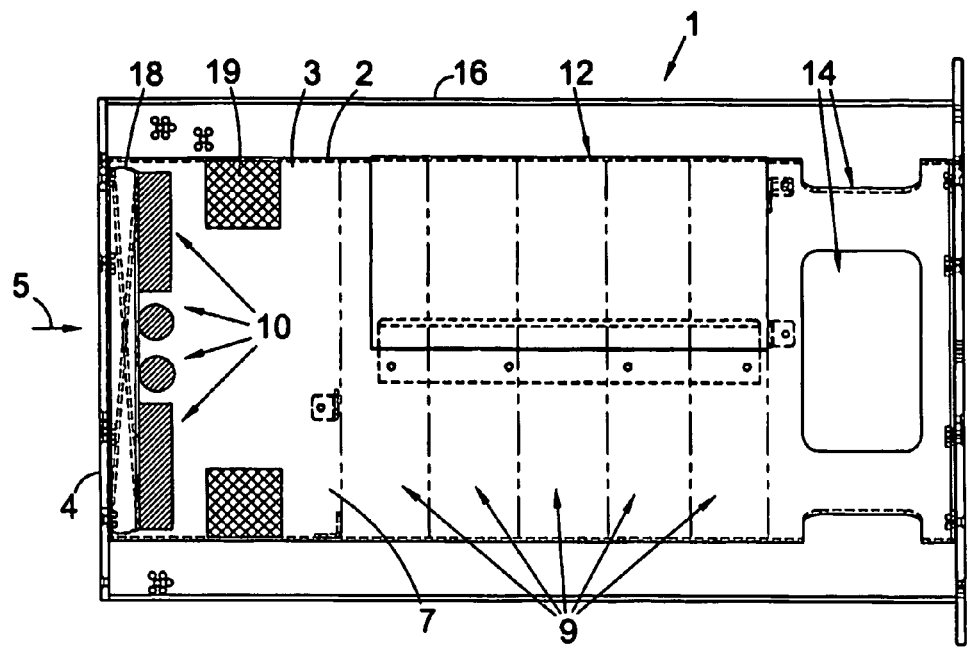

FIG. 1 shows an air filtration cartridge 1 of the invention suitable for use in the treatment of air in a forced airflow air supply system of an aircraft (not shown). The cartridge 1 comprises an inner casing 2 having an upstream stage 3 defining a chamber 4 having an inlet 5 for receiving a forced airflow 6. The chamber 4 has an outlet 7 which leads into a downstream stage 8 comprising a filter holder and mounting a stack of 10 25 mm thick high airflow electrostatic filters 9 (see FIG. 2), which are preferably 3M Filtrete™ HAF filters.

Figure 3:
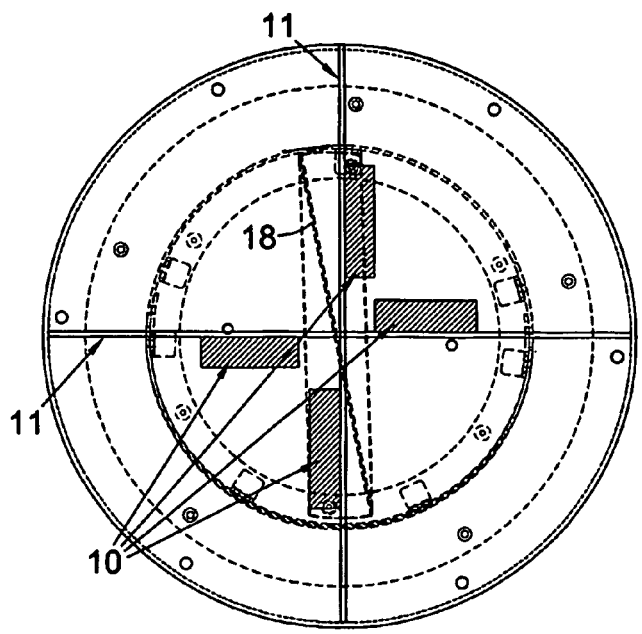

Inside the chamber 4 is mounted an array of four generally radially extending angularly distributed low power coronal discharge ozone generator devices 10, supported on insulating material struts 11 (see FIG. 3). The downstream stage 8 is provided with a removable access panel 12 for facilitating insertion and removal of the filters 9. At the downstream end portion 13 of the downstream stage 8 beyond the filters 9 are provided four circumferentially distributed exhaust openings 14 through which treated air 15 emerges directly into an annular cavity between the inner casing 2 and a perforated outer casing 16, from whence it may then pass, out 17 into the air recirculation system (not shown) for delivery back into the aircraft cabin.

The inlet 5 to the chamber 4 is provided with a flow diverter 18 for applying a twists to the incoming air flow 6, which is then further disturbed by interaction with the corona discharge device array 10. The latter are powered by suitable transformers 19 delivering 9 mA at 4 kV, each powering a pair of the corona discharge devices 10.

Figure 4:
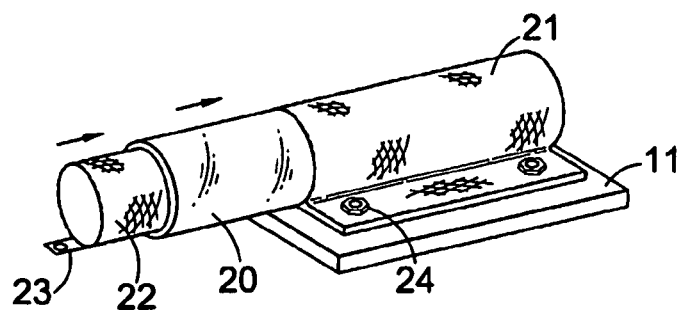

The details of the construction of the corona discharge device units 10 are shown in FIG. 4 which has been partly exploded for greater clarity. A silica glass tube dielectric 20 with a wall thickness of 0.8-1.1 mm has outer 21 and inner 22 essentially tubular stainless steel gauze electrodes. The dimensions are not critical but in this case the glass tube is approximately 63 mm long, inner electrode is formed from a 40×34 mesh number gauze of approximately 71×63 mm, and the outer electrode is formed from a coarser 24×28 mesh number gauze of approximately 133×63 mm. The inner electrode fits within the glass tube and is fitted with a spade end electrical connector 23. The outer electrode is formed into a cylinder fitting around the glass tube with a flange 24 allowing it to be fixed, together with the glass tube and inner electrode assembly, to the insulating plastic strut 11 by means of insulating nylon screws and washers and nuts 24.

The corona discharge device units 10 used have a power rating of approximately 18 W corona discharge unit operating at approximately 4 kV and 4.5 mA

Performance

The corona discharge device units described above have been tested for efficiency in various microbiological tests for killing of airborne bacteria and fungal (*Aspergillus niger*) spores and found to kill >95% at a flow rate of about 750 $m^3h^{-1}$. The output of ozone has also been tested and been found to be within the EH38 guidelines.

EXAMPLE 2

Anti-Microbial Performance of an M4/4 Device

The invention has been developed into a range of devices designed for microbiological decontamination of atmospheres. This embodiment employs closed-coupled field technology for the contained generation of an oxidising field, in tandem with electrostatic filtration of the air stream. Combining these technologies in a manner that affords a high flow-rate permits the effective treatment of large volumes of atmosphere.

M4/4 Device

This embodiment of the invention comprises four fans connected and switched so as to be progressively activated in order to provide a range of airflow rates:

Speed 1=160 $m^3$/hour Speed 2=320 $m^3$/hour

Speed 3=480 $m^3$/hour Speed 4=540 $m^3$/hour

Two modes of filtration were used in various experiments. Either a HEPA filter or an HAF (3M Filtrete™) post-filter were fitted and their relative effects compared.

Ozone Production Characteristics

The European standard for atmospheric levels of ozone is currently 0.2 ppm while, according to various literature sources the required dosage of ozone required to inactivate microbial systems, on contact, varies between 0.05 ppm and 0.4 ppm. An important aspect of this validation effort has been to demonstrate compliance of the device with European ozone emission standards, whilst additionally producing evidence of sufficient ozone generation to accommodate effective competence with regard to the task of broad scope anti-microbial activity.

A key advantage of the device is the claim that ozone generation and reactions with micro-organisms, occur contained solely within the device resulting in decontamination with no measurable emission of ozone.

Ozone Measurements

Ozone levels have been investigated employing a novel probe by which ozone production is determined by measurement of the degree of oxidation obtained with a d-□ tocopherol coating during exposure. Trials have been conducted to measure ozone production within the device and the potential for environmental accumulation during use, with and without filter in situ.

TABLE 1

Measurement of ozone production by d-α tocopherol probe oxidation with filter in place

| Run Time hours | $0^3$ ppm within treatment chamber | $0^3$ ppm within 60 $m^3$ Room |
|---|---|---|
| 0 | 24 | <0.2 |
| 6 | 103 | <0.2 |
| 12 | 94 | <0.2 |
| 18 | 107 | <0.2 |
| 24 | 102 | <0.2 |

TABLE 2

Measurement of ozone production by d-α tocopherol probe oxidation without filter in place

| Time hours | $0_3$ ppm within treatment chamber | $0_3$ ppm within 60 $m^3$ Room |
|---|---|---|
| 0 | 41 | <0.2 |
| 6 | 96 | <0.2 |
| 12 | 97 | <0.2 |

TABLE 2-continued Measurement of ozone production by d-α tocopherol probe oxidation without filter in place

| Time hours | $O_3$ ppm within treatment chamber | $O_3$ ppm within 60 m$^3$ Room |
|---|---|---|
| 18 | 104 | <0.2 |
| 24 | 106 | <0.2 |

Data indicate no significant emission of ozone from the device were detected over a 24 hour period in the operating environment. Measurements indicate that significantly higher levels of ozone are produced within the closed coupled field device than predictably are required for contact inactivation all classes of micro-organisms for which susceptibility has been published.

Microbiological Aspects of Filter Performance

Electrostatic air filtration is known to produce reduction in the levels air-borne microbial contaminants. A potential problem with stand-alone filtration devices is therefore the accumulation of possibly infective or otherwise unwanted viable contamination within the structure of the filter during life span. Trials conducted to monitor these possibilities generated the following data showing the recovery of differing classes of organism from the interior surfaces of the terminal filter during different periods of operation in waste processing room.

TABLE 3

Recovery of viable micro-organisms from electrostatic filter material after differing periods of usage

| Operation interval | TVC cm$^3$ Filter material | Moulds cm$^3$ Filter material | Yeasts cm$^3$ Filter material | *Bacillus* sp. cm$^3$ Filter material | Gram neg sp. cm$^3$ Filter material | Gram Pos sp. cm$^3$ Filter material |
|---|---|---|---|---|---|---|
| 1 day | <10 | <10 | <10 | <10 | <10 | <10 |
| 1 week | <10 | <10 | <10 | <10 | <10 | <10 |
| 1 month | <10 | <10 | <10 | <10 | <10 | <10 |
| 4 months | <10 | 30 | <10 | 20 | <10 | 80 |

Conclusions

These data demonstrate that in an environment known to have high levels of air-borne microbial contamination no significant build up of viable organisms occurred in the filtration unit up to and including three months of use. This effect may caused by impingement of residual ozone on the active surfaces, loss of viability due to dehydration in the high flow rate of air, nutrient scarcity or a combination of these and other factors. Such findings to some degree support the anti-microbial efficiency of the ozone generation system presented. More importantly these findings suggest that in respect of bacteria and fungi the filtration stage is unlikely to represent a biological hazard during replacement.

EXAMPLE 3

Single Pass Anti-Microbial Competence of M4/4 Device

The following experimental data reports on the performance of the device in relation to the reduction of single pass microbial challenges. Performance at each of four flow rates has been determined for a range of organisms with electrostatic filtration in place.

TABLE 4

M4/4 single pass performance with electrostatic filtration

| Organism | Challenge level cfu/l-$^1$ | Speed 1 Recovery cfu/l-1 | Speed 2 Recovery cfu/l-1 | Speed 3 Recovery cfu/l-1 | Speed 4 Recovery cfu/l-1 |
|---|---|---|---|---|---|
| *A. niger* | 8.80E+06 | <1 | <1 | <1 | <1 |
| *S. typhimurium* | 7.40E+06 | <1 | <1 | <1 | <1 |
| *C. albicans* | 6.00E+06 | <1 | <1 | <1 | <1 |
| *S. aureus* | 7.10E+06 | <1 | <1 | <1 | <1 |
| *B. cereus* | 2.20E+06 | <1 | <1 | <1 | 1.30E+02 |

EXAMPLE 4

Continuous Dosage Lethality with a Range of Micro-Organisms

In this series of trials a wide range of microbial types was continuously introduced at the intake section of the M4/4 device for a period of 1 hour. During the exposure time periodic measurements were taken at the output section and the levels of survivors determined. The following results were obtained.

TABLE 8

M4/4 performance: continuous input of bacteria and fungi

| Organism | Class | Mean cfu/m$^3$/Hr at input Treatment stream | Mean cfu/m$^3$/ Hr post Treatment exit stream | Mean decline Log/cfu/m$^3$/ Hr post Treatment exit stream | Apparent percentage reduction |
|---|---|---|---|---|---|
| *Escherichia coli* | Gram −ve | 2.1E+05 | 0.0E+00 | >5 | >99.999 |
| *S. tyhpimurium* | Gram −ve | 4.6E+05 | 0.0E+00 | >5 | >99.999 |
| *E. agglormerans* | Gram −ve | 3.9E+05 | 0.0E+00 | >5 | >99.999 |
| *E. gergoviae* | Gram −ve | 4.2E+05 | 0.0E+00 | >5 | >99.999 |
| *A. aerogens* | Gram −ve | 7.1E+05 | 0.0E+00 | >5 | >99.999 |
| *S. marcescens* | Gram −ve | 8.2E+05 | 0.0E+00 | >5 | >99.999 |
| *E. sakazakii* | Gram −ve | 3.4E+05 | 0.0E+00 | >5 | >99.999 |
| *E coli* 0157 H:7 | Gram −ve | 3.5E+05 | 0.0E+00 | >5 | >99.999 |

TABLE 8-continued

M4/4 performance: continuous input of bacteria and fungi

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent percentage reduction |
|---|---|---|---|---|---|
| P. aeruginosa | Gram −ve | 6.1E+05 | 0.0E+00 | >5 | >99.999 |
| P. putida | Gram −ve | 8.2E+05 | 0.0E+00 | >5 | >99.999 |
| S. aureus oxford | Gram +ve | 4.3E+05 | 0.0E+00 | >5 | >99.999 |
| S. aureus MSRA | Gram +ve | 4.8E+05 | 0.0E+00 | >5 | >99.999 |
| S. epidermidis | Gram +ve | 3.7E+05 | 0.0E+00 | >5 | >99.999 |
| M. luteus | Gram +ve | 9.0E+05 | 0.0E+00 | >5 | >99.999 |
| S. faecalis | Gram +ve | 7.3E+05 | 0.0E+00 | >5 | >99.999 |
| S. pyogenes | Gram +ve | 3.6E+05 | 0.0E+00 | >5 | >99.999 |
| B. cereus | Gram +ve | 7.1E+05 | 0.0E+00 | >5 | >99.999 |
| B. globigii | G+ve Spore | 7.9E+05 | 1.0E+01 | >5 | 99.999 |
| B. subtilis | G+ve Spore | 2.1E+05 | 3.0E+01 | >5 | 99.986 |
| B. megaterium | G+ve Spore | 6.2E+05 | 9.0E+01 | >5 | 99.985 |
| S. cerevisiea | Yeast | 4.3E+05 | 0.0E+00 | >5 | >99.999 |
| S. bailli | Yeast | 7.2E+05 | 0.0E+00 | >5 | >99.999 |
| Pichia mixed sps | Yeast | 6.3E+05 | 0.0E+00 | >5 | >99.999 |
| S. ludwigii | Yeast | 6.0E+05 | 0.0E+00 | >5 | >99.999 |
| A. niger | Mould mycelial | 6.2E+05 | 0.0E+00 | >5 | >99.999 |
| A. flavus | Mould mycelial | 7.8E+05 | 0.0E+00 | >5 | >99.999 |
| F. poea | Mould mycelial | 7.2E+05 | 0.0E+00 | >5 | >99.999 |
| P. digitatum | Mould mycelial | 6.9E+05 | 0.0E+00 | >5 | >99.999 |
| F graminerium | Mould mycelial | 4.3E+05 | 0.0E+00 | >5 | >99.999 |
| A. niger | Mould Spore | 8.2E+05 | 7.0E+01 | >5 | 99.991 |
| A. flavus | Mould Spore | 6.7E+05 | 5.0E+01 | >5 | 99.993 |
| F. poea | Mould Spore | 8.2E+05 | 0.0E+00 | >5 | >99.999 |
| P. digitatum | Mould Spore | 6.7E+05 | 0.0E+00 | >5 | >99.999 |
| F graminerium | Mould Spore | 2.9E+05 | 0.0E+00 | >5 | >99.999 |

TABLE 9

M4/4 performance: continuous input of viral particles

| Organism | Class | Mean cfu/m$^3$/Hr at input Treatment stream | Mean cfu/m$^3$/Hr post Treatment exit stream | Mean decline Log/cfu/m$^3$/Hr post Treatment exit stream | Apparent percentage reduction |
|---|---|---|---|---|---|
| CTX | SS DNA | 4.3E+12 | 8.1E+02 | >12 | >99.999 |
| ScV-L-BC | DS RNA | 9.2E+12 | 4.6E+02 | >12 | >99.999 |
| FcoV (attenuated) | SS + RNA | 7.1E+12 | 3.0E+02 | >12 | >99.999 |
| T4 Phage | DS DNA | 5.3E+12 | 7.4E+02 | >12 | >99.999 |

Conclusions

The device demonstrated a high level of competence in the inactivation of a wide range of micro-organisms including bacterial cells, bacterial spores, viral particles, mould, mould spores and yeasts. Kill efficiencies in excess of Log 12 were obtained consistently for all classes of viral particle examined, while for all other classes of organism no less than a Log 5 kill was obtained on a continuous basis. In summary, the device is highly effective at killing micro-organisms.

EXAMPLE 5

Duct-Mounted Apparatus

It has been found that one 5 W corona discharge device unit, similar to those described above, per approximately 500 m$^3$ per hour throughput of air, is suitable in clearing air of micro-organisms, odours, and smoke.

EXAMPLE 6 LEVELS OF OZONE LEAKAGE

Active and Passive Sampling

A: Active Sampling

Tests Performed

The leakage of ozone from an operating AM4 unit (190 m$^3$ h$^{-1}$ airflow, one 5 W corona discharge unit) was measured when the air filtration system was operated in 4 different modes: (i) filter in and corona discharge unit on; (ii) filter out and corona discharge unit on; (iii) filters in and corona discharge unit off, and (iv) filters out and corona discharge unit off.

The ozone levels were measured at 0, 0.5 and 1.0 m from the emitting face of the unit. The distance was measured using a meter rule and was checked at intervals during the experiment by the operator. The experiment was performed on 19 Jun. 2002 in a laboratory that was at a temperature of 22° C. The ozone measurement was performed using Gastec detection tubes (No. 18L). The 18L range provides a rapid, fully quantitative analysis of the concentration of ozone in air with an accuracy of ±25%. The manufacturer states that the minimum detectable concentration as 0.01 ppm. The Gastec tubes were purchased specifically for this work and were marked valid until May 2005. A Gastec multi-stroke gas sampling pump was used in conjunction with the tubes.

The principle of the gas tube operation is described by equation 1 below.

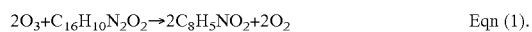
$$2O_3 + C_{16}H_{10}N_2O_2 \rightarrow 2C_8H_5NO_2 + 2O_2 \qquad \text{Eqn (1)}.$$

The ozone in air, once sucked up through the tube, bleaches the indigo ($C_{16}H_{10}N_2O_2$, blue) to form isatin ($C_8H_5NO_2$), which is white in colour. For each position, i.e. 0, 0.5 and 1.0 m from the emitting surface, (at an approximate angle of 90°) and each operational mode, a tube was placed in the pump and held in position manually. The system was left to stabilize for 5 minutes and then 10 pumps (equivalent to 1000 cm³ volume) were drawn on the hand pump. Each pump lasted an average of 30 seconds. The measurement for each combination of position and operational mode was repeated five times.

Results

The Individual Results for Each Tube are Shown in Table 18.

TABLE 18

Individual raw results (ppm) for the Gastec tubes.

| Running mode | Order[1] | Replicate results (ppm) | | | | | Mean (ppm) | Actual value[2] (ppm) |
|---|---|---|---|---|---|---|---|---|
| | | 1 | 2 | 3 | 4 | 5 | | |
| Filter in; corona on | | | | | | | | |
| 0 m | 4th | 0.1 | 0.1 | 0.1 | 0.1 | 0.1 | 0.1 | 0.05 |
| 0.5 m | 5th | 0 | 0 | 0 | 0 | 0 | 0 | 0 |
| 1.0 m | 6th | 0 | 0 | 0 | 0 | 0 | 0 | 0 |
| Filter out; corona on | | | | | | | | |
| 0 m | 3rd | <0.05 | <0.05 | <0.05 | <0.05 | <0.05 | <0.05 | <0.025 |
| 0.5 m | 7th | 0 | 0 | 0 | 0 | 0 | 0 | 0 |
| 1.0 m | 8th | 0 | 0 | 0 | 0 | 0 | 0 | 0 |
| Filter in; corona off | | | | | | | | |
| 0 m | 1st | 0 | 0 | 0 | 0 | 0 | 0 | 0 |
| 0.5 m | 11th | 0 | 0 | 0 | 0 | 0 | 0 | 0 |
| 1.0 m | 12th | 0 | 0 | 0 | 0 | 0 | 0 | 0 |
| Filter out; corona off | | | | | | | | |
| 0 m | 2nd | 0 | 0 | 0 | 0 | 0 | 0 | 0 |
| 0.5 m | 9th | 0 | 0 | 0 | 0 | 0 | 0 | 0 |
| 1.0 m | 10th | 0 | 0 | 0 | 0 | 0 | 0 | 0 |

[1]this shows the order in which the replicates where run.
[2]As 10 pumps were used, the values read from the tubes were halved as per the manufacturers instructions.

Discussion and Conclusions

The readings were very small such that the highest readings only coloured the first graduation on the Gastec tube. The highest reading was recorded when the tube was placed at the emitting surface and the filter was in and the korona was on. The next highest reading was recorded with the korona on, but the filter out. All other positions and operational combinations produced no change of colour on the Gastec tube indicating the levels of ozone, if present, were less than 0.01 ppm. The average gap in the Gastec tube through which the air is drawn was 1 mm. The analysis system used is known as active sampling. Five replicate tubes were used for each combination to help account for the potential variability in the positioning of the Gastec tube within the flow of air exiting from the air filtration system.

B: Passive Sampling

Tests Performed

The tests are were designed to determine whether a significant concentration of ozone accumulated in a confined space in which an AM4 unit operated over an 8 hour period as measured by passive sampling.

The test was performed in a room of approximately 36.75 m³ (3.5 m×3.5 m×3.0 m) receiving minimal natural light. Ozone was measure by a number of sampling cards (AFC International Inc, USA).

1. ChromAir ozone cards
2. ChromAir nitrogen cards
3. SafeAir ozone cards
4. SafeAir nitrogen dioxide cards Nitrogen dioxide is a potential positive interferent beyond 0.3 ppm with both ozone sampling cards and so its concentration was also monitored. Average room temperature 19° C. Sample cards were placed randomly on the floor, walls and suspended from the ceiling of the room. The cards were monitored for 8 hours with and without the unit operating. Monitoring was every 15 minutes for the first hour and then after a further 7 hours.

Results

Unit off:

ChromAir ozone cards: 0.08* ppm (0.01 ppm/h)
Lowest recordable concentration=background SafeAir ozone cards: no change detected Nitrogen Dioxide: none detected Unit on:

ChromAir ozone cards: 0.40 ppm (0.05 ppm/h)

SafeAir ozone cards: qualitative change indicating ozone detected

Nitrogen Dioxide: none detected
Overall ozone levels:
'Unit on'–'Unit off' values=0.04 ppm time weighted average over 8 hour period
Discussion
HSE occupational exposure limit (OEL) for ozone over an 8 hour period is 0.2 ppm and the 15 minute exposure limit is set at 0.4 ppm. The recorded ozone leakage in the experiment was therefore well within (20%) the 8 hour exposure limit.

What is claimed is:

1. An air filtration cartridge suitable for use in the treatment of air in a forced airflow air supply system having an air supply conduit provided with an in-line filtration cartridge mounting formed and arranged for releasably mounting a replaceable air filtration cartridge so that the air supply is passed through said cartridge, said cartridge comprising a casing having:
    an upstream stage defining a chamber, the chamber being defined by an earthed casing comprising a metal or a plastics material impregnated or coated with a metallic material and having an inlet for receiving a said forced airflow, in use of the cartridge, and an outlet;
    at least one low power coronal discharge ozone generator mounted inside the chamber, said at least one ozone generator being formed and arranged for generating a restricted concentration of ozone and any other reactive species formed together therewith, within an inactivating zone contained within said cartridge, through which said air flow is passed in use of said cartridge, which restricted concentration is sufficient to effectively inactivate airborne pollutant material entrained in the air flow, yet which restricted concentration decays sufficiently outside said inactivating zone so that the concentration of ozone in the cleaned air expelled from said cartridge is at a physiologically acceptable level without the use of an ozone decomposition catalyzer; and
    a downstream stage coupled to said upstream stage outlet and formed and arranged for mounting, in use of the cartridge, a high airflow electrostatic filter.

2. The cartridge of claim 1 wherein said low power corona discharge ozone generator comprises a low power corona discharge device provided with a low power high voltage output transformer.

3. The cartridge of claim 2 wherein the low power corona discharge device comprises concentric tubular metal gauze electrodes separated by a tubular strengthened glass dielectric.

4. The cartridge of claim 3 wherein the glass dielectric includes titanium dioxide strengthened borosilicate glass.

5. A cartridge according to claim 1 wherein the low power corona discharge ozone generator has a power rating of from 4 to 50 watts.

6. A cartridge according to claim 1 wherein an AC supply with a frequency in the range from 50 to 1000 Hz is used for said corona discharge ozone generator.

7. A cartridge according to claim 1 wherein an AC supply with an operating voltage in the range from 1 to 6 kV provides power to the corona discharge ozone generator.

8. A cartridge according to claim 1 wherein an AC supply provides a current in the range from 1 to 10 mA to the corona discharge ozone generator.

9. A cartridge according to claim 1 wherein a solid dielectric is used with the low power corona discharge ozone generator.

10. A cartridge according to claim 1 further comprising an array of ozone generators distributed across the airflow path through said upstream stage.

11. A cartridge according to claim 1 wherein a downstream stage filter mounting defined by the downstream stage has a depth of from 5 to 50 cms.

12. A cartridge according to claim 1 wherein said inlet is fitted with at least one filter.

13. A cartridge according to claim 12 further comprising at least one inlet filter for removing smoke.

14. A cartridge according to claim 1 wherein said downstream stage includes an annular air reservoir extending around a filter housing for said high airflow electrostatic filter, downstream of said filter, for the purpose of ensuring that the flow of air back into the air supply system is substantially unrestricted.

15. A cartridge according to claim 1 further comprising seals formed and arranged for ensuring the forced airflow is directed through said upstream and downstream stages of the cartridge.

16. A cartridge according to claim 11 wherein said filter mounting has a said high airflow electrostatic filter mounted therein.

17. A cartridge according to claim 16 wherein said filter is in the form of a stack of filter elements.

18. A method of cleaning air without the use of an ozone decomposition catalyzer, comprising:
    providing a cartridge according to claim 1 with a high airflow electrostatic filter mounted in the filter mounting thereof;
    powering the ozone generator of said cartridge so as to generate ozone in the inactivation zone of said cartridge; and
    passing a flow of said air through said inactivation zone and then through said filter.

* * * * *